United States Patent
Ryu et al.

(10) Patent No.: US 7,205,412 B2
(45) Date of Patent: Apr. 17, 2007

(54) ANTIBIOTIC ADDITIVE AND INK COMPOSITION COMPRISING THE SAME

(75) Inventors: Seung-min Ryu, Yongin (KR); Jae-hwan Kim, Suwon (KR); Jong In Lee, Suwon (KR); Dae hee Lee, Daejeon (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 652 days.

(21) Appl. No.: 10/610,525

(22) Filed: Jul. 2, 2003

(65) Prior Publication Data

US 2004/0024037 A1    Feb. 5, 2004

(30) Foreign Application Priority Data

Jul. 3, 2002  (KR) ............... 10-2002-0038470
Feb. 21, 2003 (KR) ............... 10-2003-0011124

(51) Int. Cl.
C07D 235/30 (2006.01)
C09D 11/00  (2006.01)

(52) U.S. Cl. ............... 548/113; 548/306.1; 548/307.4; 548/308.7

(58) Field of Classification Search ............... 548/113, 548/306.1, 307.4, 308.7

See application file for complete search history.

(56) References Cited

U.S. PATENT DOCUMENTS

| | | | |
|---|---|---|---|
| 4,001,423 A * | 1/1977 | Dodds | 514/388 |
| 5,019,164 A * | 5/1991 | Tomita et al. | 106/31.43 |
| 5,108,503 A | 4/1992 | Hindagolla et al. | |
| 5,641,346 A | 6/1997 | Mantell et al. | |
| 5,858,075 A | 1/1999 | Deardurff et al. | |
| 5,972,086 A | 10/1999 | Kato et al. | |
| 5,980,622 A | 11/1999 | Byers | |
| 5,990,202 A | 11/1999 | Nguyen et al. | |
| 6,039,796 A | 3/2000 | Kubota et al. | |
| 6,057,384 A | 5/2000 | Nguyen et al. | |
| 6,095,645 A | 8/2000 | Owatari et al. | |
| 7,011,700 B2 * | 3/2006 | Jung et al. | 106/31.27 |

FOREIGN PATENT DOCUMENTS

JP      52-70024    6/1977

OTHER PUBLICATIONS

Chemical Abstracts, 125:33638, 1996.*
Office Action (issue date Feb. 28, 2005) issued from Koran Intellectual Property Office with respect to Korean Patent Application No. 2003-11124 filed on Feb. 21, 2003.

* cited by examiner

Primary Examiner—Fiona T. Powers
(74) Attorney, Agent, or Firm—Staas & Halsey LLP

(57) ABSTRACT

An antibiotic additive and an ink composition including the antibiotic additive include a compound produced by binding of an antibiotic substance having the following formula (I) to a predetermined additive via a chemical reaction. The ink composition includes a colorant, a solvent and an antibiotic additive produced by binding of an antibiotic substance having the following formula (I) to a predetermined additive via a chemical reaction. The antibiotic additive prevents surface dry, improves storage stability and inhibits propagation and growth of bacteria in an ink and has excellent compatibility with a general dye or pigment

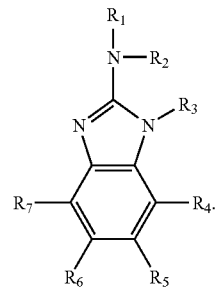

13 Claims, No Drawings

ANTIBIOTIC ADDITIVE AND INK COMPOSITION COMPRISING THE SAME

CROSS-REFERENCE TO RELATED APPLICATIONS

This application claims the benefit of Korean Application Nos. 2002-38470, filed Jul. 3, 2002 and 2003-11124, filed Feb. 21, 2003 in the Korean Intellectual Property Office, the disclosure of which is incorporated herein by reference.

BACKGROUND OF THE INVENTION

1. Field of the Invention

The present invention relates to an antibiotic additive and an ink composition comprising the same. More particularly, it relates to an antibiotic additive showing antibiotic effects provided by binding of a compound having antibiotic effects to a wetting agent or storage stabilizer in an ink composition and an ink composition comprising the same.

2. Description of the Related Art

The antibiotic additive according to the present invention and the ink composition comprising the same may be applied to, for example, coatings, paints, inks, and the like. Of them, the ink compositions for a printer, particularly ink compositions for an ink jet printer are representative. Instances of applications as an ink composition for an ink jet printer will be concretely described below.

The printing method by a printer is largely divided into two types: non-impact printing and impact printing. Ink jet printing is a non-impact printing method and has advantages such as a low noise level, as compared to the impact printing methods, and may more readily realize colors, as compared to laser beam printers.

The ink jet printing methods are of two types: continuous stream and drop-on-demand. In continuous stream ink jet methods, ink is ejected in a continuous stream under pressure through an orifice or nozzle. The ejected ink is broken up into droplets and perturbed at a fixed distance from the nozzle. The droplets, while being dispersed, are charged in accordance with digital data signals. The charged droplets pass through an electric field in which the trajectory of each droplet is adjusted to be circulated, or is directed to a gutter on a specific location of a recording medium. In a drop-on demand method, an ink droplet is expelled from a nozzle directly onto a specific location of a recording medium in accordance with digital data signals. Thus, a droplet is not formed or expelled unless it is ejected onto a recording medium.

The drop-on-demand methods are much simpler than the continuous stream systems since the drop-on-demand methods do not require ink recovery, charging or deflection. There are two types of drop-on-demand ink jet methods, one of which is the thermal ink jet type (also called bubble jet type) and the piezoelectric inkjet type.

In the thermal ink jet methods, ink is ejected using a pressure generated by expansion of bubbles formed by heating the ink. The thermal ink jet methods produce droplets having a high speed and allow a very close distance between nozzles. By introduction of the thermal ink jet methods, a printer may operate at a high speed and at low cost while having a simple structure, as compared to using the continuous stream printing methods.

On the other hand, according to the piezoelectric ink jet methods, ink is ejected under a pressure generated by a piezoelectric plate, which may dynamically transform droplets by electricity. Thus, in the piezoelectric ink jet methods, the piezoelectric plate with a relatively large size interferes with a close distance between nozzles. Also, such a physical limit of the piezoelectric plate ultimately reduces the speeds of the ink droplets. A low droplet speed severely reduces resistance to the droplet speed change and thus, affects provision of high quality prints. Further, the drop-on-demand system, when applying a piezoelectric ink jet method, has a disadvantage of a low printing speed.

Meanwhile, the dot size of the ink jet printers gets smaller, and there is a need for a high quality print at a high resolution. In order to obtain a smaller dot size, a print head of an ink jet printer is required to have a smaller nozzle opening. However, such a small nozzle opening may be readily clogged, and the performance of ink jet droplets depend on precipitations which may exert influence on sizes of the droplets. It is already known that components of an ink composition may cause nozzle clogging, and a wetting agent is usually added to inks for the ink jet printer to prevent the clogging.

Also, an ink composition for use in an ink jet printer comprises basically a colorant, a solvent and other additives. However, for an application in color printing using an ink jet printer, such an ink composition should have properties that faciliate jetting on a recording medium as intended and, after being jetted, be adsorbed or absorbed on the recording medium to form an expected image. Therefore, the ink composition comprises various additives to show proper performance in viscosity, surface tension, optical density, dot uniformity, jetting stability, drying time, bleeding, storage stability, color properties (hue, lightness, saturation), affinity to a printer head and a recording medium, smear fastness, water fastness of an image, and the like. It has been proposed to use a nitrogen-containing heterocyclic compound such as 2-pyrrolidone, N-methyl-2-pyrrolidone, 1,3-dimethyl-2-imidazolidinone as an additive to realize the storage stability of an ink composition (U.S. Pat. Nos. 5,108,503; 5,858,075; 5,980,622; 5,990,202; 6,057,384; 5,641,346; 5,972,086; 6,039,796; 6,095,645). According to the disclosures of the above listed patents, when a nitrogen-containing heterocyclic compound such as 2-pyrrolidone, N-methyl pyrrolidone, N-methyl-2-pyrrolidone, 1,3-dimethyl-2-imidazolidinone is used as an additive, it is possible to obtain effects of improving storage stability, wettability and drying properties.

When a dye is used as a colorant in an ink composition for an ink jet printer, the water fastness and light fastness of the ink are impaired. Therefore, use of such a dye is limited. On the other hand, where a pigment is used as a colorant, the water fastness and the light fastness of the ink are superior to a water fastness and a light fastness of an ink using a dye. Meanwhile, an ink composition comprising a dye or a pigment as a colorant has problems of deterioration in ink properties due to propagation of bacteria and thus, storage stability. Therefore, it has been proposed to add a special antibiotic to suppress the propagation and growth of bacteria. However, the antibiotics added in an ink composition may bond to other additives in the ink composition to form a macromolecule, which significantly increases the nozzle clogging by ink coagulation and makes it difficult to ensure uniformity of the ink. Also, when an antibiotic which can inhibit such side effects is used, problems occur in that storage stability for a long period of time may be deteriorated, owing to the weak antibiotic properties, and optimal color properties cannot be attained since it is difficult to select a dye or a pigment with an excellent compatibility with the antibiotic.

SUMMARY OF THE INVENTION

Therefore, the present invention has been made in view of the above problems, and it is an aspect of the present invention to provide an antibiotic additive which prevents drying the surface, improves storage stability, inhibits propagation and growth of bacteria in an ink and has excellent compatibility with a general dye or pigment. The antibiotic additive is produced by binding an antibiotic compound to a wetting agent or a storage stabilizer added in an ink composition via a chemical reaction, and the invention includes an ink composition comprising the antibiotic additive.

To accomplish the above aspects, according to the present invention, an antibiotic additive comprises a compound produced by chemically reacting an antibiotic substance having a structure of the following formula (I) with a predetermined additive.

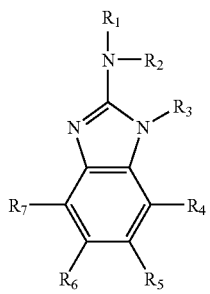

(I)

in which, $R_1$ is selected from the group consisting of a hydrogen atom, a hydroxy group, an amino group, a carboxyl group and salts thereof, a sulfonic acid group and salts thereof, and a phosphoric acid group and salts thereof; and $R_2$, $R_3$, $R_4$, $R_5$, $R_6$ and $R_7$ are each independently selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

The substituted or unsubstituted $C_1$ to $C_{30}$ alkyl group may include $C_1$ to $C_{30}$ straight or branched alkyl radicals.

Examples of the alkyl radical include, but are not limited to, methyl, ethyl, n-propyl, isopropyl, n-butyl, isobutyl, sec-butyl, t-butyl, pentyl, iso-amyl, hexyl, heptyl, octyl, nonyl, decyl and dodecyl.

Preferably, the substituted $C_1$ to $C_{30}$ alkyl group, substituted $C_1$ to $C_{30}$ alkenyl group, substituted $C_1$ to $C_{30}$ alkynyl group, substituted $C_1$ to $C_{30}$ heteroalkyl group, substituted $C_6$ to $C_{30}$ aryl group, substituted $C_6$ to $C_{30}$ arylalkyl group, substituted $C_6$ to $C_{30}$ heteroaryl group and substituted $C_6$ to $C_{30}$ heteroarylalkyl group each independently has at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a $C_1$ to $C_{20}$ alkyl group, a $C_1$ to $C_{20}$ alkenyl group, a $C_1$ to $C_{20}$ alkynyl group, a $C_1$ to $C_{20}$ heteroalkyl group, $C_6$ to $C_{20}$ aryl group, a $C_6$ to $C_{20}$ arylalkyl group, a $C_6$ to $C_{20}$ heteroaryl group and a $C_6$ to $C_{30}$ heteroarylalkyl group.

The additive which reacts with the antibiotic substance of the formula (I) is a wetting agent or a storage stabilizer.

Preferably, the wetting agent includes at least one selected from the group consisting of alcohols, diols, triols, polyols, polyethylene glycols and polypropylene glycols.

Preferably, the storage stabilizer includes at least one selected from nitrogen-containing compounds such as substituted or unsubstituted 2-pyrrolidone, N-methyl pyrrolidone, pyridine, imidazole, piperidine, 2-pyrrolidinone, primary amine, secondary amine, tertiary amine, amide, lactone, and lactam. The substituted nitrogen-containing compounds have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl groups, $C_1$ to $C_{20}$ alkenyl groups, $C_1$ to $C_{20}$ alkynyl groups, $C_1$ to $C_{20}$ heteroalkyl groups, $C_6$ to $C_{20}$ aryl groups, $C_6$ to $C_{20}$ arylalkyl groups, $C_6$ to $C_{20}$ heteroaryl groups and $C_6$ to $C_{20}$ heteroarylalkyl groups.

Also, the antibiotic additive according to the present invention may comprise at least one or both of antibiotic additives with any one of the above-described wetting agents chemically bonded thereto, and antibiotic additives with any one of the above-described storage stabilizers chemically bonded thereto.

In accordance with a second aspect of the present invention, an ink composition comprises a colorant, a solvent and an antibiotic additive. The antibiotic additive comprises a compound produced by chemically reacting an antibiotic substance having a structure of the following formula (I) with a prescribed additive,

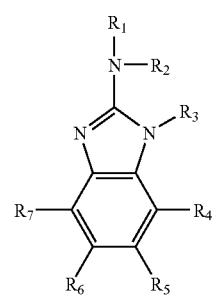

(I)

in which, $R_1$ is any one selected from the group consisting of a hydrogen atom, a hydroxy group, an amino group, a carboxyl group and salts thereof, a sulfonic acid group and salts thereof, and a phosphoric acid group and salts thereof; and $R_2$, $R_3$, $R_4$, $R_5$, $R_6$ and $R_7$ are each independently any one selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

The substituted or unsubstituted $C_1$ to $C_{30}$ alkyl group may include $C_1$ to $C_{30}$ straight or branched alkyl radicals.

Examples of the alkyl radical include, but are not limited to, methyl, ethyl, n-propyl, isopropyl, n-butyl, isobutyl, sec-butyl, t-butyl, pentyl, iso-amyl, hexyl, heptyl, octyl, nonyl, decyl and dodecyl.

Here, it is preferred that the substituted $C_1$ to $C_{30}$ alkyl group, substituted $C_1$ to $C_{30}$ alkenyl group, substituted $C_1$ to $C_{30}$ alkynyl group, substituted $C_1$ to $C_{30}$ heteroalkyl group, substituted $C_6$ to $C_{30}$ aryl group, substituted $C_6$ to $C_{30}$ arylalkyl group, substituted $C_6$ to $C_{30}$ heteroaryl group and substituted $C_6$ to $C_{30}$ heteroarylalkyl group each independently have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a $C_1$ to $C_{20}$ alkyl group, a $C_1$ to $C_{20}$ alkenyl group, a $C_1$ to $C_{20}$ alkynyl group, a $C_1$ to $C_{20}$ heteroalkyl group, a $C_6$ to $C_{20}$ aryl group, a $C_6$ to $C_{20}$ arylalkyl group, a $C_6$ to $C_{20}$ heteroaryl group and a $C_6$ to $C_{20}$ heteroarylalkyl group.

The additive which reacts with the antibiotic substance of the formula (I) is a wetting agent or storage stabilizer.

Preferably, the wetting agent includes at least one selected from the group consisting of alcohols, diols, triols, polyols, polyethylene glycols and polypropylene glycols.

Preferably, the storage stabilizer includes at least one selected from nitrogen-containing compounds such as substituted or unsubstituted 2-pyrrolidone, N-methyl pyrrolidone, pyridine, imidazole, piperidine, 2-pyrrolidinone, primary amine, secondary amine, tertiary amine, amide, lactone, and lactam. The substituted nitrogen-containing compounds have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl groups, $C_1$ to $C_{20}$ alkenyl groups, $C_1$ to $C_{20}$ alkynyl groups, $C_1$ to $C_{20}$ heteroalkyl groups, $C_6$ to $C_{20}$ aryl groups, $C_6$ to $C_{20}$ arylalkyl groups, $C_6$ to $C_{20}$ heteroaryl groups and $C_6$ to $C_{20}$ heteroarylalkyl groups.

Also, the antibiotic additive according to the present invention may comprise at least one or both of antibiotic additives with any one of the above-described wetting agents chemically bonded thereto, and antibiotic additives with any one of the above-described storage stabilizers chemically bonded thereto.

In the ink composition comprising the antibiotic additive according to the present invention, the antibiotic additive is preferably used in an amount in the range of 0.1 weight parts to 30 weight parts to 100 weight parts of the ink composition.

The solvent which can be used in the composition of the present invention is water alone or in combination with an organic solvent.

When a mixture of water and an organic solvent is used, the content of the organic solvent is preferably in the range of 5 weight parts to 50 weight parts to 100 weight parts of the ink composition.

The organic solvent includes any one selected from the group consisting of alcoholic solvents such as methyl alcohol, ethyl alcohol, n-propyl alcohol, isopropyl alcohol, n-butyl alcohol, sec-butyl alcohol, t-butyl alcohol and isobutyl alcohol; ketone solvents such as acetone, methylethyl ketone and diacetone alcohol; ester solvents such as ethylacetate and ethyl lactate; polyhydric alcohol solvents such as ethylene glycol, diethylene glycol, triethylene glycol, propylene glycol, butylene glycol, 1,4-butanediol, 1,2,4-butanetriol, 1,5-pentanediol, 1,2,6-hexanetriol, hexylene glycol, glycerol, glycerol ethoxylate and trimethylpropane ethoxylate; alkyl ether solvents such as ethylene glycol monomethyl ether, ethylene glycol monoethyl ether, diethylene glycol methyl ether, diethylene glycol ethyl ether, triethylene glycol monomethyl ether and triethylene glycol monoethyl; nitrogen-containing solvents such as 2-pyrrolidone, N-methyl pyrrolidone and N-methyl-2-pyrrolidone; and sulfur-containing solvents such as dimethyl sulfoxide, tetramethylenesulfone and thioglycol.

When the colorant in the ink composition according to the present invention is a pigment, the ink composition preferably further comprises a dispersant.

The dispersant preferably includes any one selected from the group consisting of phenol polymers which are modified with polyvinyl alcohol, cellulose polymer and ethylene oxide, ethylene oxide polymers, propylene oxide polymers, sodium polyacrylate solutions, modified polyacryl resin solutions, low molecular polycarboxylic acid polymer alkylol ammonium salt solution and multi-functional polymer alkylol ammonium solution; polyether siloxane copolymer; and hydrophilic AB polymers (A-B structure) and BAB polymers (B-A-B structure), in which A is a hydrophobic homopolymer or copolymer of a substituted or unsubstituted $C_1$ to $C_{30}$ acrylic monomer and B is a hydrophilic polymer or copolymer of a substituted or unsubstituted $C_1$ to $C_{30}$ acrylic monomer. Particularly, the AB polymer is any one selected from acrylic acid/acrylate copolymers and methacrylic acid/methacrylate copolymers, and the BAB polymer is an acrylic acid/polydialkylsiloxane/acrylate block copolymer.

According to the present invention, the ink composition may further comprise a viscosity modifier. When the ink composition comprises a viscosity modifier, the content of the viscosity modifier is preferably in the range of 0.1 weight parts to 10.0 weight parts to 100 weight parts of the ink composition. Also, more preferably, the viscosity modifier includes any one selected from the group consisting of casein, carboxymethylcellulose, polyethylene glycol, polypropylene glycol, polyvinylpyrrolidone, polyethyleneimine and polyvinyl alcohol.

Also, the ink composition according to the present invention may further comprise a surfactant.

When the ink composition further comprises a surfactant, it is preferred that the surfactant includes, but is not limited to, an anionic surfactant such as $C_1$ to $C_{1000}$ alkylcarboxylates, $C_1$ to $C_{1000}$ alkylsulfonates, $C_1$ to $C_{1000}$ alkylsulfonic ester salts and $C_1$ to $C_{1000}$ alkylbenzene sulfonates; and nonionic surfactants such as polyoxyethylene alkyl ethers in which the alkyl group is one of $C_1$ to $C_{1000}$, polyoxyethylene alkylphenyl ethers in which the alkyl group is one of $C_1$ to $C_{1000}$, polyoxyethylene secondary alcohol ethers, polyoxyethylene-oxypropylene block copolymers, polyglycerin fatty acid esters and sorbitan fatty acid esters.

Also, the content of the surfactant is preferably in the range of 0.1 weight parts to 5 weight parts to 100 weight parts of the ink composition.

DETAILED DESCRIPTION OF THE PREFERRED EMBODIMENTS

Now, the present invention is described in detail as follows. The present invention is directed to an antibiotic addictive comprising an antibiotic substance having a particular functional group and a predetermined additive bonded thereto via a chemical reaction, and an ink composition comprising the antibiotic additive.

The antibiotic additive according to the present invention comprising an antibiotic substance and an additive bonded thereto via a chemical reaction shows antibiotic effects while maintaining intrinsic functions of the additive. The antibiotic substance which is used in the propagation of the antibiotic additive according to the present invention is a compound of the following formula (II), which is also called "benzoimidazole":

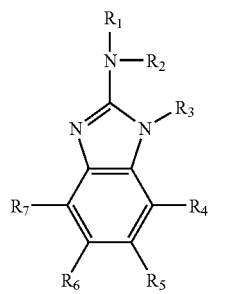

(II)

in which, $R_1$ is selected from the group consisting of a hydrogen atom, a hydroxy group, an amino group, a carboxyl group and salts thereof, a sulfonic acid group and salts thereof and a phosphoric acid group and salts thereof; and $R_2$, $R_3$, $R_4$, $R_5$, $R_6$ and $R_7$ are each independently any one selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

More preferred compounds represented by the formula (II) which can be used as the antibiotic substance in the present invention are compounds represented by the following formula (III):

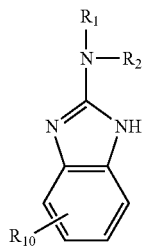

in which, $R_1$ is selected from the group consisting of a hydrogen atom, a hydroxy group, an amino group and a carboxyl group; and $R_2$ and $R_{10}$ are each independently selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

The R group in the formulae (II) and (III) is more specifically described below.

The alkyl group includes $C_1$ to $C_{30}$ straight or branched radicals, preferably $C_1$ to $C_{20}$ straight or branched radicals. More preferably, it is an alkyl group containing a $C_1$ to $C_{12}$ radical. Examples of such radicals include methyl, ethyl, n-propyl, isopropyl, n-butyl, isobutyl, sec-butyl, t-butyl, pentyl, iso-amyl, hexyl, heptyl, octyl, nonyl, decyl and dodecyl, but are not limited thereto.

Also, the alkyl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The alkenyl group or alkynyl group refers to one that contains a carbon-carbon double bond or carbon-carbon triple bond at the middle or end of an alkyl group. Examples thereof include ethylene, propylene, butylene, hexylene, acetylene and the like. The alkenyl group or alkynyl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The heteroalkyl group refers to one that contains any one selected from the group consisting of a nitrogen atom, a sulfur atom, an oxygen atom and a phosphorus atom. Examples thereof include methoxy, ethoxy, propoxy, butoxy and t-butoxy. Examples of heteroalkyl group with a substituent include haloalkoxy radicals such as fluoromethoxy, chloromethoxy, trifluoromethoxy, trifluoroethoxy, fluoroethoxy and fluoropropoxy. The heteroalkyl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The aryl group refers to a carbocyclic aromatic system of $C_6$ to $C_{30}$ containing at least one ring, in which the ring is attached or fused by the pendant method. The term 'aryl' refers to aromatic radicals of similar types such as phenyl, naphthyl, indane and biphenyl. The aryl group is preferably phenyl or naphthyl. Also, the aryl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The arylalkyl group refers to ones that have part of the hydrogen atoms in the aryl group substituted with a low alkyl radical, such as, methyl, ethyl or propyl. Examples thereof include benzyl, phenylethyl, phenylpropyl, phenylisopropyl and the like. The arylalkyl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The heteroaryl group refers to a univalent monocyclic or bicyclic aromatic radical containing at least one hetero atom selected from the group consisting of N, O, P and S and ring carbon atoms of $C_3$ to $C_{30}$. Also, the term heteroaryl refers to a univalent monocyclic or bicyclic aromatic radical having a hetero atom in a ring which is to form an oxidized or quaternized salt, such as N-oxide or a quaternary salt. Examples thereof include thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and N-oxides of the foregoing (for example, pyridyl N-oxide, quinolinyl N-oxide, etc.) and quaternary salts of the foregoing; but are not limited thereto.

The heteroaryl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The term heteroarylalkyl group refers to one that has part of the hydrogen atoms in the heteroaryl group substituted with an alkyl group. The heteroarylalkyl group may have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl group, $C_1$ to $C_{20}$ alkenyl group, $C_1$ to $C_{20}$ alkynyl group, $C_1$ to $C_{20}$ heteroalkyl group, $C_6$ to $C_{20}$ aryl group, $C_6$ to $C_{20}$ arylalkyl group, $C_6$ to $C_{20}$ heteroaryl group and $C_6$ to $C_{20}$ heteroarylalkyl group.

The substituents of $R_1, R_2, \ldots R_7$ and $R_{10}$ used according to the present invention, such as the alkylene group, alkenylene group, alkynylene group, heteroalkylene group, arylene group, arylalkylene group, heteroarylene group, and heteroarylalkylene group also may be defined as for the alkyl group, alkenyl group, alkynyl group, heteroalkyl group, aryl group, arylalkyl group, heteroaryl group and heteroarylalkyl group. However, the substituents of $R_1$, $R_2, \ldots R_7$ and $R_{10}$ are different due to being inserted in the middle of the bond between compounds, but are not connected to the end of the compound.

The amount of the antibiotic additive which is used in the ink composition for an ink jet printer according to the present invention is preferably in the range of 0.1 weight parts to 30 weight parts to 100 weight parts of the ink composition. When the added amount of the antibiotic additive is greater than 30 weight parts, the viscosity of the composition is not controlled. When the added amount of the antibiotic additive is less than 0.1 weight parts, the composition does not show antibiotic effects.

The antibiotic additive according to the present invention is a compound produced by a chemical reaction of an antibiotic substance of the formulae II or III with a predetermined additive, that is, a benzo imidazole derivative.

In a preferred embodiment of the antibiotic additive according to the present invention, the predetermined additive which is bonded to the antibiotic substance by a chemical reaction is one that is added as a wetting agent to the ink composition. An example of such a chemical reaction is shown in the following Reaction Scheme (I).

Reaction Scheme I

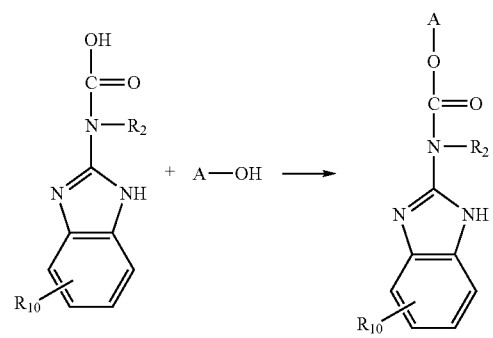

In the Scheme (I), the reagent A-OH is a wetting agent and the compound of the left side is a compound of the formula (III), in which $R_1$ is a carboxyl group and $R_2$ and $R_{10}$ are each independently any one selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

In the Scheme (I), the carboxyl group of the antibiotic substance is reacted with a hydroxy group of the wetting agent via esterification to produce an antibiotic additive. —COOA in the produced antibiotic additive performs intrinsic functions of the wetting agent, and the remaining structure serves as an antibiotic.

The wetting agent which may be used in the present invention includes any one selected from the group consisting of alcohol, diol, triol, polyol, polyethylene glycol and polypropylene glycol, or a mixture of one or two or more thereof. The wetting agent may be selected considering reactivity, stability of a product of the reaction, and the like. Therefore, the wetting agent which may be used to provide the antibiotic additive according to the present invention is not limited to the above-described compounds.

Also, in another preferred embodiment of the antibiotic additive according to the present invention, the prescribed additive which is bonded to the antibiotic substance by a chemical reaction is one that is added as a storage stabilizer to the ink composition. An example of such a chemical reaction is shown in the following Reaction Scheme (II).

Reaction Scheme II

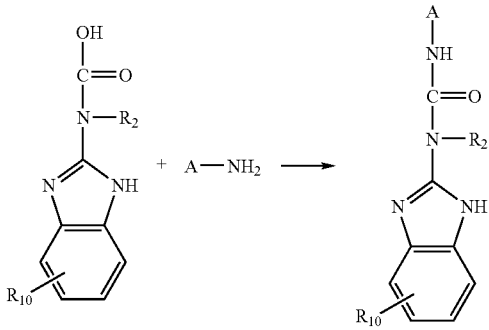

In the Scheme (II), the reagent A-NH2 is a storage stabilizer and the compound of the left side is a compound of the formula (III), in which R1 is a carboxyl group and R2 and R10 are each independently any one selected from the group consisting of a hydrogen atom, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted $C_6$ to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

In the Scheme (II), the carboxyl group of the antibiotic substance is reacted with an amino group of the storage stabilizer via amidation to produce an antibiotic additive. —CONHA in the produced antibiotic additive performs intrinsic functions of the storage stabilizer, and the remaining structure serves as an antibiotic.

The storage stabilizer which may be used in the present invention includes any one selected from the group consisting of substituted or unsubstituted 2-pyrrolidone, N-methyl pyrrolidone, pyridine, imidazole, piperidine, 2-pyrrolidinone, primary amine, secondary amine, tertiary amine, amide, lactone and lactam, or a mixture of one or two or more thereof. The storage stabilizer can be selected considering reactivity, stability of a product of the reaction, and the like. Therefore, the storage stabilizer which may be used to provide the antibiotic additive according to the present invention is not limited to the above-described compounds.

The antibiotic additive according to the present invention may be a compound produced by binding of an antibiotic substance to a wetting agent via a chemical reaction, a compound produced by binding of an antibiotic substance to a storage stabilizer via a chemical reaction, or a mixture thereof.

In another aspect, the present invention is directed to an ink composition comprising the antibiotic additive. Therefore, the antibiotic additive contained in the ink composition comprising the antibiotic additive according to the present invention also has the characteristics described above.

The ink composition comprising the antibiotic additive according to the present invention contains an aqueous liquid medium as a solvent. As the aqueous liquid medium, water may be used alone or in combination with at least one organic solvent. When an organic solvent is used, the total content of the organic solvent is preferably in the range of 5 weight parts to 50 weight parts to 100 weight parts of the ink composition.

The amounts of water and an organic solvent in the aqueous liquid medium depend on various factors including properties of an intended ink composition such as viscosity, surface tension, and/or transparency of the ink. Such properties may vary according to ink-jet print methods and medium types on which the ink is printed. In the case of the ink composition according to the present invention, an added amount of an organic solvent is preferably in the foregoing range, considering such properties.

The organic solvent which can be used in an aqueous medium according to the present invention is any one selected from the group consisting of alcohol solvents such as methyl alcohol, ethyl alcohol, n-propyl alcohol, isopropyl alcohol, n-butyl alcohol, sec-butyl alcohol, t-butyl alcohol and isobutyl alcohol; ketone solvents such as acetone, methylethyl ketone and diacetone alcohol; ester solvents such as ethylacetate and ethyl lactate; polyhydric alcohol solvents such as ethylene glycol, diethylene glycol, triethylene glycol, propylene glycol, butylene glycol, 1,4-butanediol, 1,2,4-butanediol, 1,5-pentanediol, 1,2,6-hexanetriol, hexylene glycol, glycerol, glycerol ethoxylate and trimethylpropane ethoxylate; low alkyl ether solvents such as ethylene glycol, monomethyl ether, ethylene glycol monoethyl ether, diethylene glycol methyl ether, diethylene glycol ethyl ether, triethylene glycol monomethyl ether and triethylene glycol monoethyl ether; nitrogen-containing compound solvents such as 2-pyrrolidone, N-methyl pyrrolidone and N-methyl-2-pyrrolidone; and sulfur-containing compound solvents such as dimethyl sulfoxide, tetramethylenesulfone and thioglycol, but is not limited thereto.

When a pigment is used as a colorant in the ink composition comprising the antibiotic additive according to the present invention, the composition may further comprise a dispersant for dispersion stability of the colorant. A usable dispersant is not particularly limited. That is, dispersants having a high molecular weight such as block copolymers which may limit the properties and the stability of an ink when they are directly contained in the ink composition may be used as a dispersant in the ink composition.

Examples of the dispersant having a low molecular weight and a simple structure include any one selected from the group consisting of polyvinyl alcohols (PVA), cellulosic polymers (cellulosics), phenolic polymers modified with ethylene oxide (ethylene oxide modified phenols), ethylene oxide/propylene oxide polymers, sodium polyacrylate solutions (TEGO, disperse 715W), modified polyacryl resin solutions (TEGO, disperse 735W), low molecular weight polycarboxylic acid polymer alkylol ammonium salt solutions (BYK-CHEMIE, DISPERBYK) and multi-functional polymer alkylol ammonium salt solutions (BYK-CHEMIE, DISPERBYK-181), or a mixture thereof; but are not limited thereto.

Examples of the dispersant having a high molecular weight and a complex structure are as follows. Siloxanes such as polyether siloxane copolymer (TEGO, Wet KL 245/Wet 260) may be used. Also, hydrophilic AB polymers or BAB polymers having an A-B or B-A-B structure, respectively, may be used, in which A is a hydrophobic homopolymer or copolymer of a substituted or unsubstituted $C_1$ to $C_{30}$ acrylic monomer and B is a hydrophilic polymer or copolymer of a substituted or unsubstituted $C_1$ to $C_{30}$ acrylic monomer. Examples of the AB polymer or BAB polymer include acrylic acid/acrylate copolymer, methacrylic acid/methacrylate copolymer and acrylic acid/ polydialkylsiloxane/acrylate block copolymer, or a mixture thereof. However, the foregoing is only for illustration of dispersants having a high molecular weight and a complex structure, not for limitation.

The content of the dispersant used in the present invention is preferably in the range of 1 weight parts to 20 weight parts to 100 weight parts of the ink composition. When the content of the dispersant is within the foregoing range, excellent dispersion effects may be obtained, preventing coagulation of a pigment.

The ink composition according to the present invention may further comprise other additives such as a viscosity modifier, a surfactant, a metal oxide and the like, as needed.

The viscosity modifier is a substance to control viscosity so that the ink jetting may be performed smoothly. According to the present invention, as the viscosity modifier, casein or carboxymethylcellulose can be used. The content of the viscosity modifier is preferably in the range of 0.1 weight parts to 5.0 weight parts to 100 weight parts of the ink composition.

The surfactant is a substance to stabilize the ink jetting performance of a nozzle by controlling surface tension of the ink composition. As the surfactant, an anionic surfactant or a nonionic surfactant may be used.

Examples of the anionic surfactant which may be used in the present invention includes any one selected from the group consisting of $C_1$ to $C_{1000}$ alkylcarboxylates, $C_1$ to $C_{1000}$ alkylsulfonates, $C_1$ to $C_{1000}$ alkylsulfonic ester salts and $C_1$ to $C_{1000}$ alkylbenzene sulfonates or mixtures thereof. Preferably, the anionic surfactants include any one selected from the group consisting of $C_{10}$ to $C_{200}$ alkylcarboxylates, $C_{10}$ to $C_{200}$ alkylsulfonic ester salts, $C_{10}$ to $C_{200}$ alkylsulfonates and $C_{10}$ to $C_{200}$ alkylbenzene sulfonates, or mixtures thereof.

Examples of the nonionic surfactant which may be used in the present invention include any one selected from the group consisting of polyoxyethylene alkyl ethers, in which the alkyl group is of $C_1$ to $C_{1000}$, polyoxyethylene alkylphenyl ethers, in which the alkyl group is of $C_1$ to $C_{1000}$, polyoxyethylene secondary alcohol ethers, polyoxyethylene-oxypropylene block copolymers, polyglycerin fatty acid esters and sorbitan fatty acid esters, or mixtures thereof. Preferably, the nonionic surfactants include any one selected from the group consisting of polyoxyethylene alkyl ethers, in which the alkyl group is of $C_{10}$ to $C_{200}$, polyoxyethylene alkyl phenyl ethers, in which the alkyl group is of $C_{10}$ to $C_{200}$, polyoxyethylene secondary alcohol ethers, polyoxyethylene-oxypropylene block copolymers, polyglycerin fatty acid esters and sorbitan fatty acid esters, or mixtures thereof.

The content of the surfactant is preferably in the range of 0.1 weight parts to 5 weight parts to 100 weight parts of the ink composition.

A method of producing an ink composition of the composition as described above is described below.

First, one prepares the antibiotic additive according to the present invention, wherein the antibiotic additive comprises:

a compound produced by binding an antibiotic substance to a wetting agent via a chemical reaction, a compound produced by binding an antibiotic substance to a storage stabilizer via a chemical reaction, or a mixture thereof.

Next, a colorant and the antibiotic additive previously prepared are added to an aqueous liquid medium along with a dispersant, a viscosity modifier, a surfactant and the like. The mixture is then sufficiently stirred in a stirrer until it is homogenous. The resulting mixture is filtered with a 0.45 µm or a 0.8 µm filter to obtain an ink composition containing the antibiotic additive according to the present invention.

Now, the present invention will be explained in detail using preferred embodiments.

EXAMPLES

Example 1

Preparation of Antibiotic Additive 27.6 g of glycerin and 18.0 g of a carbendazim derivative of the following formula (IV) were added to 300 ml of DMSO in a 500 ml Erlenmeyer flask while stirring to form a solution. To the resulting solution, 1 or 2 glass beads were added, and 30 ml of conc. sulfuric acid was slowly added. The Erlenmeyer flask was connected to a reflux condenser. The reaction was allowed to proceed sufficiently for at least 8 hours at 80° C., after which it was cooled to room temperature. An excessive amount of methanol was added to form crystals. The crystals were then filtered by suction. In order to remove impurities including unreacted substances in the obtained crystals, the crystals were dissolved in DMSO, and an excessive amount of methanol was added thereto for recrystallization. The crystals were filtered by suction and dried in an oven to give 24.5 g of an antibiotic additive of the following formula (V).

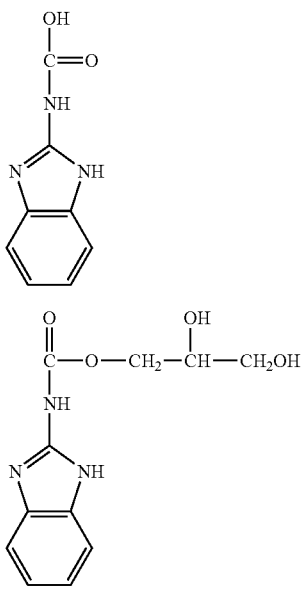

(IV)

(V)

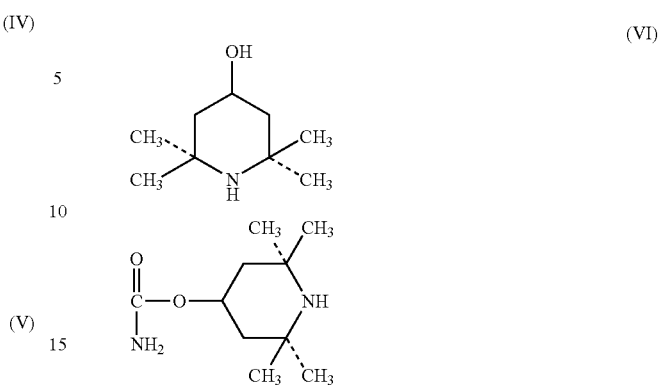

(VI)

Preparation of Ink Composition

In order to prepare an ink composition containing the antibiotic additive of the formula (V), each of the following ingredients was mixed and stirred in a stirrer for at least 30 minutes until the mixture was homogeneous. Then, the mixture was filtered with a 0.45 μm filter to give the ink composition containing the antibiotic additive.

| | |
|---|---|
| C.I. Direct Black 168 | 3.5 g |
| Antibiotic additive of the Formula (V) | 8.0 g |
| Isopropyl alcohol | 2.0 g |
| 2-Pyrrolidone | 10.0 g |
| Distilled water | 76.5 g |

Example 2

Preparation of Antibiotic Additive 18.4 g of a carbendazim derivative of the following formula (IV) was added to 300 ml of DMSO in a 500 ml Erlenmeyer flask while stirring to form a solution. 7.1 g of SOCl2 was added thereto and reacted for at least 1 hour at room temperature to form solution A. 57.2 g of 2, 2, 6, 6-tetramethyl-4-piperidinol of the following formula (VI) dissolved in 200 ml of DMSO was added to solution A, and 1 or 2 glass beads were also added. The Erlenmeyer flask was connected to a reflux condenser. The reaction was allowed to proceed sufficiently for at least 6 hours at 80° C., after which it was cooled to room temperature. An excessive amount of methanol was added to form crystals. The crystals were then filtered by suction. In order to remove impurities, including unreacted substances in the obtained crystals, the crystals were dissolved in DMSO, and an excessive amount of methanol was added thereto for recrystallization. The crystals were filtered by suction and dried in an oven to give 12.6 g of an antibiotic additive of the following formula (VII).

Preparation of Ink Composition

In order to prepare an ink composition containing the antibiotic additive of the formula (VII), each of the following ingredients was mixed and stirred in a stirrer for at least 30 minutes until the mixture was homogeneous. Then, the mixture was filtered with a 0.45 μm filter to give the ink composition containing the antibiotic additive.

| | |
|---|---|
| Antibiotic additive of the formula (VII) | 6.0 g |
| Isopropyl alcohol | 2.0 g |
| Propylene glycol | 8.0 g |
| Polyethylene glycol | 4.0 g |
| Distilled water | 76 g |

Example 3

Preparation of antibiotic additive] solution C. 12.9 g of 2-pyrrolidone-5-carboxylic acid of the following formula (IX) dissolved in 200 ml of DMSO was added to solution C1 and 1 or 2 glass beads were also added. The Erlenmeyer flask was connected to a reflux condenser. The reaction was allowed to proceed sufficiently for at least 6 hours at 80° C., after which it was cooled to room temperature. An excessive amount of methanol was added to form crystals. The crystals were then filtered by suction. In order to remove impurities, including unreacted substances in the obtained crystals, the crystals were dissolved in DMSO, and an excessive amount of methanol was added thereto for recrystallization. The crystals were filtered by suction and dried in an oven to give 12.5 g of an antibiotic additive of the following formula (X).

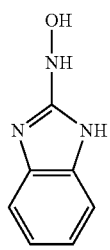

(VIII)

-continued

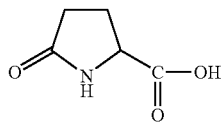
(IX)

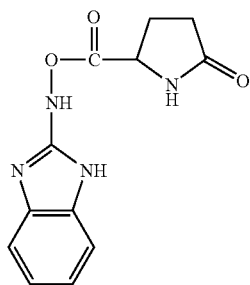
(X)

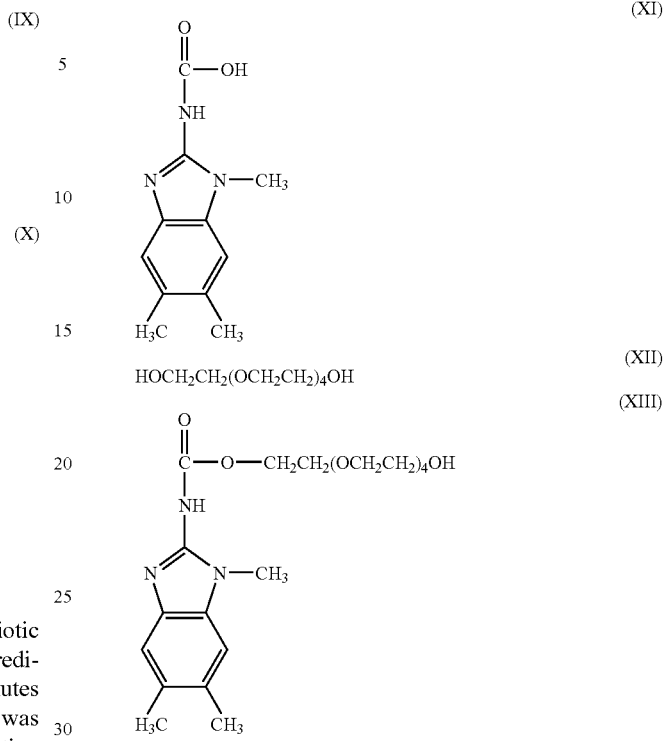

(XI)

HOCH₂CH₂(OCH₂CH₂)₄OH (XII)

(XIII)

Preparation of Ink Composition

To prepare an ink composition containing the antibiotic additive of the formula (X), each of the following ingredients was mixed and stirred in a stirrer for at least 30 minutes until the mixture was homogeneous. Then, the mixture was filtered with a 0.45 μm filter to give the ink composition containing the antibiotic additive.

| | |
|---|---|
| C.I. Direct Black 199 | 4.0 g |
| Antibiotic additive of the formula (X) | 8.0 g |
| Isopropyl alcohol | 4.0 g |
| 1,5-Pentanediol | 10.0 g |
| Distilled water | 74 g |

Example 4

Preparation of Antibiotic Additive 45 g of a carbendazim derivative of the following formula (XI) was added to 100 ml of DMSO in a 500 ml Erlenmeyer flask while stirring to form a solution. 7.7 g of SOCl2 was added thereto and reacted for at least 1 hour at room temperature to form solution E. 47.6 g of ethylene glycol derivatives of the following formula (XII) dissolved in 200 ml of DMSO was added to solution E, and 1 or 2 glass beads were also added. The Erlenmeyer flask was connected to a reflux condenser. The reaction was allowed to proceed sufficiently for at least 6 hours at 80° C., after which it was cooled to room temperature. An excessive amount of methanol was added to form crystals. The crystals were then filtered by suction. In order to remove impurities, including unreacted substances in the obtained crystals, the crystals were dissolved in DMSO, and an excessive amount of methanol was added thereto for recrystallization. The crystals were filtered by suction and dried in an oven to give 75.2 g of an antibiotic additive of the following formula (XIII).

Preparation of Ink Composition

To prepare an ink composition containing the antibiotic additive of the formula (XIII), each of the following ingredients was mixed and stirred in a stirrer for at least 30 minutes until the mixture was homogeneous. Then, the mixture was filtered with a 0.45 μm filter to give the ink composition containing the antibiotic additive.

| | |
|---|---|
| C.I. Reactive Red 180 | 4.5 g |
| Antibiotic additive of the formula (XIII) | 10 g |
| Ethanol | 3.0 g |
| N-methyl pyrrolidone | 6.0 g |
| Distilled water | 76.5 g |

Example 5

Preparation of Antibiotic Additive 25.8 g of pyrrolidone carboxylic acid of the formula (IX) and 24.2 g of a carbendazim derivative of the following formula (XIV) were added to 300 ml of DMSO in a 500 ml Erlenmeyer flask while stirring to form a solution. To the resulting solution, 1 or 2 glass beads were also added and 30 ml of conc. sulfuric acid was slowly added. The Erlenmeyer flask was connected to a reflux condenser. The reaction was allowed to proceed sufficiently for at least 8 hours at 80° C., after which it was cooled to room temperature. An excessive amount of methanol was added to form crystals. The crystals were then filtered by suction. In order to remove impurities including unreacted substances in the obtained crystals, the crystals were dissolved in DMSO, and an excessive amount of methanol was added thereto for recrystallization. The crystals were filtered by suction and dried in an oven to give 26.0 g of an antibiotic additive of the following formula (XV).

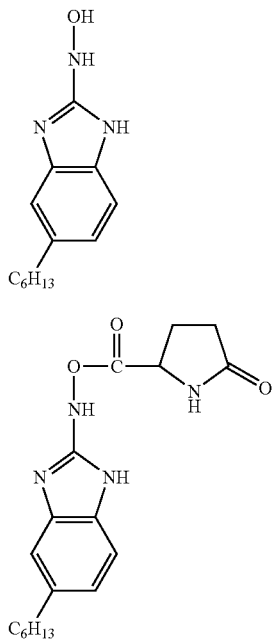

(XIV)

(XV)

Preparation of Ink Composition

To prepare an ink composition containing the antibiotic additive of the formula (XV), each of the following ingredients was mixed and stirred in a stirrer for at least 30 minutes until the mixture was homogeneous. Then, the mixture was filtered with a 0.45 μm filter to give the ink composition containing the antibiotic additive.

| | |
|---|---|
| C.I. Acid Yellow 23 | 3.0 g |
| Antibiotic additive of the formula (XV) | 8.0 g |
| Ethylene glycol | 4.0 g |
| Propylene glycol | 5.0 g |
| Distilled water | 80.0 g |

Example 6

Preparation of Antibiotic Additive

The antibiotic additive of this example was the compound of the formula (XIII) prepared using the same process as described for the preparation of the antibiotic additive in Example 4.

Preparation of Ink

To prepare an ink composition containing the antibiotic additive of the formula (XIII), the following ingredients were mixed.

| | |
|---|---|
| Carbon black | 4.0 g |
| Styrene/acrylate copolymer | 4.0 g |
| Monoethanolamine | 0.5 g |
| Antibiotic additive of the formula (XIII) | 8.0 g |

-continued

| | |
|---|---|
| 2-pyrrolidone | 4.0 g |
| Polyethylene glycol | 2.0 g |
| Isopropyl alcohol | 4.0 g |
| Distilled water | 73.5 g |

After mixing the above ingredients, the resulting mixture was dispersed under the following conditions.
Dispersing apparatus: Sand mill
Dispersing medium: Glass bead (Diameter 1 μm)
Applied level of dispersing medium: 50% (V/V)
Dispersing Time: 3 Hours
The dispersion was centrifuged at a speed of 12,000 rpm for 20 minutes to remove large particles and to finally obtain a dispersion ink having a particle size of 0.1 μm or less.

Example 7

Preparation of Antibiotic Additive

The antibiotic additive of this example was the compound of the formula (V), prepared using the same process as described for the preparation of the antibiotic additive in Example 1.

Preparation of Ink

To prepare an ink composition containing the antibiotic additive of the formula (V), the following ingredients were mixed.

| | |
|---|---|
| Phthalocyanine blue | 4.5 g |
| Styrene/acrylate copolymer | 3.5 g |
| Triethanolamine | 0.3 g |
| Antibiotic additive of the formula (V) | 10.0 g |
| N-methyl pyrrolidone | 6.0 g |
| Polyethylene glycol | 2.0 g |
| Isopropyl alcohol | 3.0 g |
| Distilled water | 70.7 g |

After mixing the above ingredients, the resulting mixture was dispersed under the following conditions.
Dispersing apparatus: Sand mill
Dispersing medium: Glass bead (Diameter 1 μm)
Applied level of dispersing medium: 50% (V/V)
Dispersing time: 3 hours
The dispersion was centrifuged at a speed of 12,000 rpm for 20 minutes to remove large particles and finally to obtain a dispersion ink having a particle size of 0.1 μm or less.

Comparative Examples

Comparative Example 1

Ink was prepared using the same procedure as described in Example 1, except that 4 g of ethylene glycol and 6 g of diethylene glycol were used instead of the antibiotic additive of the formula V in Example 1.

Comparative Example 2

Ink was prepared using the same procedure as described in Example 2, except that 6.0 g of N-methyl pyrrolidone was used instead of the antibiotic additive of the formula VII in Example 2.

Comparative Example 3

Ink was prepared using the same procedure as described in Example 3, except that 8.0 g of 2-pyrrolidone was used instead of the antibiotic additive of the formula X in Example 3.

Comparative Example 4

Ink was prepared using the same procedure as described in Example 4, except that 10.0 g of diethylene glycol and 0.2 g of BIT as antibiotics were used instead of the antibiotic additive of the formula XIII in Example 4.

Comparative Example 5

Ink was prepared using the same procedure as described in Example 1, except that 8.0 g of caprolactam and 0.1 g of BIT as antibiotics were used instead of the antibiotic additive of the formula XV in Example 5.

Comparative Example 6

Ink was prepared using the same procedure as described in Example 6, except that 8.0 g of diethylene glycol was used instead of the antibiotic additive of the formula XIII in Example 6.

Comparative Example 7

Ink was prepared using the same procedure as described in Example 7, except that 3.0 g of ethylene glycol, 7.0 g of diethylene glycol and 0.1 g of BIT as antibiotics were used instead of the antibiotic additive of the formula V in Example 7.

Evaluations

Evaluation 1

This evaluation was conducted to examine whether precipitates formed when inks prepared according to Example 1 to Example 7 and Comparative Example 1 to Comparative Example 7 were left for a predetermined period of time. The results are shown in Table 1. The experiment was carried out by putting 100 ml of each ink of Example 1 to Example 7 and Comparative Example 1 to Comparative Example 7, respectively, in fourteen different 250 ml bottles. The bottles were sealed and stored in a water bath at 60° C. After a predetermined period of time, the bottom of each bottle was examined for precipitate formation. The results are shown in Table 1.

TABLE 1

| Ink | Precipitate formation according to storage time (0, x) | | | | | | |
|---|---|---|---|---|---|---|---|
| | 7 days | 14 days | 30 days | 60 days | 120 days | 180 days | 360 days |
| Example 1 | 0 | 0 | 0 | 0 | 0 | 0 | 0 |
| Example 2 | 0 | 0 | 0 | 0 | 0 | 0 | 0 |
| Example 3 | 0 | 0 | 0 | 0 | 0 | 0 | 0 |
| Example 4 | 0 | 0 | 0 | 0 | 0 | 0 | 0 |
| Example 5 | 0 | 0 | 0 | 0 | 0 | 0 | 0 |
| Example 6 | 0 | 0 | 0 | 0 | 0 | 0 | 0 |
| Example 7 | 0 | 0 | 0 | 0 | 0 | 0 | 0 |
| Comparative Example 1 | 0 | 0 | 0 | x | x | x | x |
| Comparative Example 2 | 0 | 0 | x | x | x | x | x |
| Comparative Example 3 | 0 | 0 | x | x | x | x | x |
| Comparative Example 4 | x | x | x | x | x | x | x |
| Comparative Example 5 | x | x | x | x | x | x | x |
| Comparative Example 6 | 0 | 0 | x | x | x | x | x |
| Comparative Example 7 | x | x | x | x | x | x | x |

0: No precipitates observed,
x: Precipitates observed.

As seen from the results of the above Table 1, in the inks comprising the antibiotics of Example 1 to Example 7 according to the present invention, no precipitate by the antibiotic additive according to the present invention was formed. On the other hand, for the inks comprising the antibiotics of Comparative Example 1 to Comparative Example 3 and Comparative Example 6, although there was no precipitate observed during a short time of storage, precipitates and fungi were observed in a long-time storage. In the inks of Comparative Example 4, Comparative Example 5 and Comparative Example 7, where antibiotic BIT was added, precipitates were formed from the beginning of the experiment. From these results, it was noted that the antibiotics additives prepared in Example 1 to Example 7 according to the present invention have effective compatibility with other components in the ink compositions, while showing antibiotic effects in the ink compositions.

Evaluation 2

This evaluation was conducted to examine whether nozzle clogging occurs when inks prepared according to Example 1 to Example 7 and Comparative Example 1 to Comparative Example, each were contained in a different cartridge. The results are shown in Table 2. The experiment was carried out by putting 50 ml of each ink of Example 1 to Example 7 and Comparative Example 1 to Comparative Example 7, respectively in fourteen different Lexmark cartridges. The cartridges were left at room temperature. After a predetermined period of time, a pattern was printed using the cartridges on a Lexmark printer to examine the nozzle clogging.

TABLE 2

| Ink | Nozzle clogging (0, Δ, x) | | | | | | |
|---|---|---|---|---|---|---|---|
| | 1 day | 3 days | 7 days | 14 days | 21 days | 28 days | 60 days |
| Example 2 | 0 | 0 | 0 | 0 | 0 | 0 | 0 |
| Example 3 | 0 | 0 | 0 | 0 | 0 | 0 | 0 |
| Example 4 | 0 | 0 | 0 | 0 | 0 | 0 | 0 |
| Example 5 | 0 | 0 | 0 | 0 | 0 | 0 | 0 |
| Example 6 | 0 | 0 | 0 | 0 | 0 | 0 | 0 |
| Example 7 | 0 | 0 | 0 | 0 | 0 | 0 | 0 |
| Comparative Example 1 | 0 | 0 | Δ | x | x | x | x |
| Comparative Example 2 | 0 | 0 | Δ | x | x | x | x |
| Comparative Example 3 | 0 | 0 | Δ | x | x | x | x |
| Comparative Example 4 | x | x | x | x | x | x | x |
| Comparative Example 5 | x | x | x | x | x | x | x |
| Comparative Example 6 | 0 | 0 | Δ | x | x | x | x |
| Comparative Example 7 | x | x | x | x | x | x | x |

0: No nozzle clogging,
Δ: Partial nozzle clogging,
x: nozzle clogging of a large part As seen from the results of the above Table 2, when the inks of Example 1 to Example 7 according to the present invention were contained, and left, in ink cartridges for a long period of time, no nozzle clog occurred. On the other hand, for the inks of Comparative Example 1 to Comparative Example 7, some or most of the cartridges showed nozzle clog, which indicates that they are not stable. Thus, it was noted that the antibiotics additives prepared in Example 1 to Example 7 according to the present invention have effective compatibility with other components, in the ink compositions while showing the intrinsic properties of the additives added as a wetting agent or a storage stabilizer in the ink compositions.

Evaluation 3

The halo zone test was used to measure antibiotic effects of the ink compositions of Examples and Comparative Examples. The halo zone test was conducted as follows. First, potato dextrose agar medium was prepared in a sterilized petri dish with a diameter of 10 cm. Aspergillus niger spores were applied in a thin layer on OHP films printed with each ink prepared in Example 1 to Example 7 and Comparative Example 1 to Comparative Example 3 and Comparative Example 6 without a dye or pigment. Then, 20 μl of distilled water was dropped on the OHP films printed with the inks which had been prepared without a colorant.

The films were left in a clean bench under ultraviolet rays for 1 hour and then, placed at the center of the agar media upon which Aspergillus niger spores had been coated. The dishes were incubated in a incubator at 30° C. for 72 hours. The growth of Aspergillus niger was observed with the naked eye. For the inks comprising the antibiotic additives of Example 1 to Example 7, the transparent area was maintained since the Aspergillus fungus could not grow. On the other hand, for the inks comprising the antibiotic additives of Comparative Example 1 to Comparative Example 3 and Comparative Example 6, the surfaces of the dishes were not clear since the Aspergillus fungus had grown and propagated. Therefore, it was noted that the antibiotic additives of Example 1 to Example 7 showed antibiotic effects and the ink compositions comprising Example 1 to Example 7 also have excellent antibiotic effects.

The dishes were measured for transmittancy and the results are shown in Table 3, below. "Examples" represents the inks of Example 1 to Example 7 and "Comparative Examples" represents the inks of Comparative Example 1 to Comparative Example 3 and Comparative Example 6.

TABLE 3

| Ink | Transmittancy (% T) before incubation | Transmittancy (% T) after incubation | Apparent transmittancy after incubation |
|---|---|---|---|
| Examples | 80 | 80 | Transparent |
| Comparative Examples | 79 | 51 | Opague |

As seen from the Table 3, the ink compositions comprising the antibiotic additives of Example 1 to Example 7 did not show a significant change in transmittancy since the fungus level did not increase after incubation. On the other hand, the inks of Comparative Example 1 to Comparative Example 3 and Comparative Example 6 showed a reduction in transmittancy due to the fungus propagation.

As described above, according to the present invention, an antibiotic additive bonds a wetting agent or a storage stabilizer which is commercially used in an ink composition to a compound having antibiotic effects. Also, an ink composition includes the antibiotic additive. Therefore, an antibiotic additive shows antibiotic effects while maintaining the intrinsic properties of an additive, and an ink composition includes the antibiotic additive. When a commercially available antibiotic is added to an ink composition, the storage stability of the ink is unreliable. However, according to the present invention an ink composition comprises an antibiotic additive with excellent storage stability which may be stored for a long period of time without precipitation.

Although the preferred embodiments of the present invention have been disclosed and explained for illustrative purposes, the present invention is not limited thereto. Those skilled in the art will appreciate that various modifications, additions and substitutions are possible, without departing from the scope and spirit of the invention as disclosed in the accompanying claims.

What is claimed is:

1. An antibiotic additive comprising a compound produced by chemically reacting an antibiotic substance having a structure of the following formula (I) with a predetermined additive,

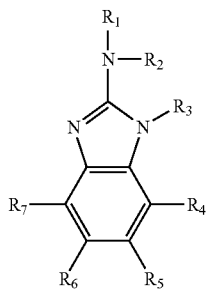

(I)

in which, $R_1$ is any one selected from the group consisting of a hydrogen atom, a hydroxy group, an amino group, a sulfonic acid group and salts thereof, and a phosphoric acid group and salts thereof; and $R_2$, $R_3$, $R_4$, $R_5$, $R_6$ and $R_7$ are each independently any one selected from the group consisting of, a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a substituted or unsubstituted $C_1$ to $C_{30}$ alkyl group, a substituted or unsubstituted $C_1$ to $C_{30}$ alkenyl group, a substituted or unsubstituted $C_1$ to $C_{30}$ alkynyl group, a substituted or unsubstituted $C_1$ to $C_{30}$ heteroalkyl group, a substituted or unsubstituted C6 to $C_{30}$ aryl group, a substituted or unsubstituted $C_6$ to $C_{30}$ arylalkyl group, a substituted or unsubstituted $C_6$ to $C_{30}$ heteroaryl group and a substituted or unsubstituted $C_6$ to $C_{30}$ heteroarylalkyl group.

2. The antibiotic additive according to claim 1, wherein the alkyl group includes a $C_1$ to $C_{30}$ straight or branched alkyl radical.

3. The antibiotic additive according to claim 1, wherein the substituted $C_1$ to $C_{30}$ alkyl group, the substituted $C_1$ to $C_{30}$ alkenyl group, the substituted $C_1$ to $C_{30}$ alkynyl group, the substituted v heteroalkyl group, the substituted $C_6$ to $C_{30}$ aryl group, the substituted $C_6$ to $C_{30}$ arylalkyl group, the substituted $C_6$ to $C_{30}$ heteroaryl group, and the substituted $C_6$ to $C_{30}$ heteroarylalkyl group each independently have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, a $C_1$ to $C_{20}$ alkyl group, a $C_1$ to $C_{20}$ alkenyl group, a $C_1$ to $C_{20}$ alkynyl group, a $C_1$ to $C_{20}$ heteroalkyl group, a $C_6$ to $C_{20}$ aryl group, a $C_6$ to $C_{20}$ arylalkyl group, a $C_6$ to $C_{20}$ heteroaryl group and a $C_6$ to $C_{20}$ heteroarylalkyl group.

4. The antibiotic additive according to claim 1, wherein the predetermined additive is a wetting agent.

5. The antibiotic additive according to claim 4, wherein the wetting agent comprises at least one selected from the group consisting of alcohols, diols, triols, polyols, polyethylene glycols and polypropylene glycols.

6. The antibiotic additive according to claim 1, wherein the predetermined additive is a storage stabilizer.

7. The antibiotic additive according to claim 6, wherein the storage stabilizer comprises at least one selected from the group consisting of substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

8. The antibiotic additive according to claim 7, wherein the substituted nitrogen-containing compounds have at least one hydrogen atom substituted with any one selected from the group consisting of a halogen atom, a hydroxy group, a nitro group, a cyano group, an amino group, an amidino group, a hydrazine group, a hydrazone group, a carboxyl group and salts thereof, a sulfonic acid group and salts thereof, a phosphoric acid group and salts thereof, $C_1$ to $C_{20}$ alkyl groups, $C_1$ to $C_{20}$ alkenyl groups, $C_1$ to $C_{20}$ alkynyl groups, $C_1$ to $C_{20}$ heteroalkyl groups, $C_6$ to $C_{20}$ aryl groups, $C_6$ to $C_{20}$ arylalkyl groups, $C_6$ to $C_{20}$ heteroaryl groups and $C_6$ to $C_{20}$ heteroarylalkyl groups.

9. The antibiotic additive according to claim 4, wherein the antibiotic additive comprises at least one selected from the group consisting of alcohols, diols, triols, polyols, polyethylene glycols, polypropylene glycols, substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

10. The antibiotic additive according to claim 5, wherein the antibiotic additive comprises at least one selected from the group consisting of alcohols, diols, triols, polyols, polyethylene glycols, polypropylene glycols, substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

11. The antibiotic additive according to claim 6, wherein the antibiotic additive comprises at least one selected from the group consisting of alcohols, diols, triols, polyols, polyethylene glycols, polypropylene glycols, substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

12. The antibiotic additive according to claim 7, wherein the antibiotic additive comprises at least one selected from the group consisting of alcohols, diols, triols, polyols, polyethylene glycols, polypropylene glycols, substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

13. The antibiotic additive according to claim 8, wherein the antibiotic additive comprises at least one selected from the group consisting of alcohols, diols, triols, polyols, polyethylene glycols, polypropylene glycols, substituted or unsubstituted 2-pyrrolidone, N-methyl pyrrolidone, pyridine, imidazole, piperidine, 2-pyrrolidinone, primary amines, secondary amines, tertiary amines, amides, lactones and lactams.

* * * * *

UNITED STATES PATENT AND TRADEMARK OFFICE
CERTIFICATE OF CORRECTION

| | | |
|---|---|---|
| PATENT NO. | : 7,205,412 B2 | Page 1 of 1 |
| APPLICATION NO. | : 10/610525 | |
| DATED | : April 17, 2007 | |
| INVENTOR(S) | : Seung-min Ryu et al. | |

It is certified that error appears in the above-identified patent and that said Letters Patent is hereby corrected as shown below:

Column 25, Line 31, change "C6" to --$C_6$--.

Signed and Sealed this

Thirty-first Day of July, 2007

JON W. DUDAS
*Director of the United States Patent and Trademark Office*